US006572875B2

(12) United States Patent
Neurath et al.

(10) Patent No.: US 6,572,875 B2
(45) Date of Patent: Jun. 3, 2003

(54) BIODEGRADABLE MICROBICIDAL VAGINAL BARRIER DEVICE

(75) Inventors: Alexander Robert Neurath, New York, NY (US); Nathan Strick, Oceanside, NY (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/966,924

(22) Filed: Sep. 28, 2001

(65) Prior Publication Data

US 2002/0076430 A1 Jun. 20, 2002

Related U.S. Application Data

(60) Provisional application No. 60/244,415, filed on Oct. 30, 2000.

(51) Int. Cl.[7] ............................. A61F 6/06; A61F 13/02; A61F 6/14; A61K 9/14
(52) U.S. Cl. ........................ 424/430; 424/431; 424/432; 424/434; 424/435; 424/436; 424/443; 424/494
(58) Field of Search ................................. 424/430, 431, 424/432, 434, 435, 436, 443, 494

(56) References Cited

U.S. PATENT DOCUMENTS

| | | | |
|---|---|---|---|
| 4,360,013 A | 11/1982 | Barrows | |
| 5,863,553 A | 1/1999 | Britton et al. | |
| 5,985,313 A | 11/1999 | Neurath et al. | |
| 6,165,493 A | 12/2000 | Neurath et al. | |

OTHER PUBLICATIONS

Neurath, A.R., Strick, N., Li, Y.–Y., Jiang, S., "Design of a 'Microbicide' for Prevention of Sexually Transmitted Diseases Using 'Inactive' Pharmaceutical Excipients", *Biologicals*, 27, 11–21, (1999).

Li, Y.–Y., Mandeville R., Richard, L., "In vitro Activity of a Cellulose Acetate Phthalate Topical Cream Against Organisms Associated with Bacterial Vaginosis", *J. Antimicrob. Chemother.*, 45, 713–714.

Manson, K.H., Wyand, M.S., Miller, C., Neurath, A.R., "The Effects of a Cellulose Acetate Phthalate Topical Cream on Vaginal Transmission of SIV in Rhesus Monkeys", *Antimicrobial Agents & Chemotherapy*, 44, 3199–3202.

Gyotoku, T., Aurelian, L., Neurath, Neurath, A.R., "Cellulose Acetate Phthalate (CAP): An 'Inactive' Pharmaceutical Excipient With Antiviral Activity in the Mouse Model of Genital Herpesvirus Infection", *Antiviral Chemistry & Chemotherapy*, 10, 327–332.

Shihata, A., "The Clinical Application of Basic Anatomy & Physiology in Microbicide Development", *Microbicides 2000*, Mar. 13–16, 2000.

Shihata, A.A., "The FemCap: A New Contraceptive Choice", *Eur. J. Contracept. Reprod. Health Care*, 3(3), pp. 160–166, (1988).

*Primary Examiner*—Carlos Azpuru
(74) *Attorney, Agent, or Firm*—Frishauf, Holtz, Goodman & Chick, P.C.

(57) ABSTRACT

An intravaginal bio-erodible microbicidal barrier device. The device comprises (a) at least one micronized compound selected from the group consisting of cellulose acetate phthalate and hydroxypropylmethylcellulose phthalate, and (b) at least one water soluble or water dispersible cellulose compound selected from the group consisting of hydroxypropylmethylcellulose, methylcellulose, hydroxyethylcellulose, hydroxypropylcellulose, hydroxyethylmethylcellulose, hydroxyethylethylcellulose and hydroxypropylethylcellulose. The device is prepared by a combination of foaming, freezing and freeze-drying processes.

20 Claims, 6 Drawing Sheets

BIODEGRADABLE MICROBICIDAL VAGINAL BARRIER DEVICE

CROSS REFERENCE TO RELATED APPLICATION

The present application claims the benefit of Provisional Application Ser. No. 60/244,415 filed Oct. 30, 2000, for which priority under 35 USC 119(e) is claimed.

BACKGROUND OF THE INVENTION

1. Field of the Invention

The present invention concerns a biodegradable vaginal barrier device. More particularly, the present invention concerns a bio-erodible microbicidal vaginal sponge made from hydroxypropylmethylcellulose phthalate and/or cellulose acetate phthalate.

2. Background Information

Applicants have previously reported that cellulose acetate phthalate ("CAP") and hydroxypropylmethylcellulose phthalate ("HPMCP") prevent infection by the human immunodeficiency virus type 1 (HIV-1). Additional studies showed that CAP also blocked infection by several herpesviruses (Neurath, A. R., Strick, N., Li, Y. -Y., Jiang, S., "Design of a 'Microbicide' for Prevention of Sexually Transmitted Diseases Using 'Inactive' Pharmaceutical Excipients", *Biologicals*, 27, 11–21, (1999); U.S. Pat. No. 5,985,313; U.S. Pat. No. 6,165,493). CAP formulated into creams was shown to inactivate HIV-1, several herpesviruses as well as nonviral sexually transmitted disease (STD) pathogens (Neurath, A. R., Strick, N., Li, Y. -Y., Jiang, S., "Design of a 'Microbicide' for Prevention of Sexually Transmitted Diseases Using 'Inactive' Pharmaceutical Excipients", *Biologicals*, 27, 11–21, (1999); U.S. Pat. No. 5,985,313). The formulated CAP also inactivated bacteria associated with bacterial vaginosis (Neurath, A. R., Li, Y. -Y., Mandeville R., Richard, L., "In vitro Activity of a Cellulose Acetate Phthalate Topical Cream Against Organisms Associated with Bacterial Vaginosis", *J. Antimicrob. Chemother.*, 45, 713–714). Results of experiments in animal models indicated that CAP formulations prevented vaginal infections by the simian immunodeficiency virus (SIV) of macaques and by herpesvirus type 2 (HSV-2) of mice (In press: Manson, K. H., Wyand, M. S., Miller, C., Neurath, A. R., "The Effects of a Cellulose Acetate Phthalate Topical Cream on Vaginal Transmission of SIV in Rhesus Monkeys", *Antimicrobial Agents & Chemotherapy*; Guotoku, T., Aurelian, L., Neurath, A. R., "Cellulose Acetate Phthalate (CAP): An 'Inactive' Pharmaceutical Excipient With Antiviral Activity in the Mouse Model of Genital Herpesvirus Infection", *Antiviral Chemistry & Chemotherapy*, 10, 327–332). Cumulatively these results indicate that formulations of CAP represent preferred microbicides for prevention of sexual transmission of a variety of STD pathogens.

To minimize the probability of conception, as well as of sexual transmission of HIV-1 and other STD pathogens, it appears critical to combine chemical and mechanical barriers (Shihata, A., "The Clinical Application of Basic Anatomy & Physiology in Microbicide Development", *Microbicides* 2000, Mar. 13–16, 2000, p. 29). The combinations of mechanical and chemical barriers in use at this time are based on solid mechanical devices combined with added detergents, Nonoxynol-9 ("N-9") and other ingredients. Examples of such devices are as follows: Protectaid™ sponge (Axcan Ltd.), the Today Sponge™ (Allendale Pharmaceuticals, Inc., Allendale, N.J.) and the FemCapT™ (Shihata, A. A., "The FemCap: A New Contraceptive Choice", *Eur. J. Contracept. Reprod. Health Care,* 3(3), pp. 160–166, (1998)). The disadvantage of these devices is that they have to be removed after use and either discarded (sponges), contributing to waste disposal problems, or cleaned for reuse (FemCap™), an impractical alternative for developing countries with scarce clean water supplies. Another disadvantage of these devices is the use of N-9 as a chemical barrier, since N-9 has been shown recently to increase the risk of sexual transmission of HIV-1 instead of blocking it. For all these reasons, alternative devices without these disadvantages are needed.

To avoid one of the above problems, such as the necessity to remove the device after use, a bio-erodible contraceptive suppository also expected to have microbicidal properties, has been described by Britton, P. et al. (U.S. Pat. No. 5,863,553). The Britton et al. device disperses or dissolves after use and therefore does not need to be removed. However the Britton et al. device still has the following disadvantages: (1) it uses N-9 as an added ingredient to provide contraceptive or microbicidal activity and (2) the device uses gelatine as a major ingredient to assure mechanical stability and ease of insertion. Gelatine is generally an undesirable animal derived product, which may potentially transmit spongiform encephalopathies (i.e., mad cow disease, Creuzfeldt-Jakob-Disease). For this reason, gelatine derived from animals susceptible to spongiform encephalopathies is not recommended, if avoidable, for medicinal use.

Devices with built-in contraceptive and microbicidal activity were disclosed by T. H. Barrows in U.S. Pat. No. 4,360,013. The Barrows devices are based on acidic polymers providing a low pH expected to be lethal to viruses, microorganisms and semen. However one of the proposed materials, oxidized cellulose (Oxycel) is prohibitively expensive and is not rapidly biodegradable. The general disadvantage of the acidic polymers listed in U.S. Pat. No. 4,360,013 is that the acidic functionalities would be neutralized in the presence of semen/seminal fluid. The neutralized polymers lack antiviral or antimicrobial activity.

SUMMARY OF THE INVENTION

It is an object of the present invention to provide a biodegradable microbicidal vaginal barrier device.

It is a further object of the present invention to furnish a bio-erodible microbicidal device for the prevention of sexually transmitted diseases.

It is a still further object of the present invention to provide a biodegradable vaginal sponge with built-in microbicidal activity.

The present invention satisfies the above objects and provides further objects, aims and advantages.

The present invention thus concerns an intravaginal bio-erodible-microbicidal barrier device comprising:

(a) at least one micronized compound selected from the group consisting of cellulose acetate phthalate and hydroxyoropylmethylcellulose phthalate, and (b) at least one water soluble or water dispersible cellulose compound selected from the group consisting of hydroxypropylmethylcellulose, methylcellulose, hydroxyethylcellulose, hydroxypropylcellulose, hydroxyethylmethylcellulose, hydroxyethylethylcellulose and hydroxypropylethylcellulose.

The cellulose acetate phthalate can be contained in an "AQUATERIC" composition which also contains poloxamers and acelyated monoglycerides.

The present invention also relates to a method of making an intravaginal bio-erodible microbicidal barrier device comprising:

(a) providing at least one micronized compound selected from the group consisting of cellulose acetate phthalate and hydroxypropylmethylcellulose phthalate;

(b) adding to the at least one micronized compound, an aqueous solution of at least one water soluble or water dispersible cellulose compound selected from the group consisting of hydroxypropylmethylcellulose, methylcellulose, hydroxyethylcellulose, hydroxypropylcellulose, hydroxyethylmethylcellulose, hydroxyethylethylcellulose and hydroxypropylethylcellulose, to form a suspension;

(c) foaming the suspension from step (b) to form a foam;

(d) disposing the foam from step (c) into a mold and freezing the foam to form a frozen foam; and (e) freeze-drying the frozen foam from step (d) to remove water.

The present invention also is directed to another method of making an intravaginal bio-erodible microbicidal barrier device comprising:

(a) preparing a first solution and a second solution, the first solution comprising at least one water soluble or water dispersible cellulose compound selected from the group consisting of hydroxypropylmethylcellulose, methylcellulose, hydroxyethylcellulose, hydroxypropylcellulose, hydroxyethylmethylcellulose, hydroxyethylethylcellulose and hydroxypropylethylcellulose, suspended or dissolved in water; the second solution comprising at least one compound selected from the group consisting of cellulose acetate phthalate and hydroxypropylmethylcellulose phthalate, dissolved in at least one organic solvent;

(b) combining the first solution and the second solution to result in an emulsion in which the cellulose acetate phthalate or the hydroxypropylmethylcellulose phthalate is in a micronized form;

(c) foaming the emulsion from step (b) to form a foam;

(d) disposing the foam from step (c) into a mold and freezing the foam to form a frozen foam; and (e) freeze-drying the frozen foam from step (d) to remove water and to remove the organic solvent.

The other ingredients in the "AQUATERIC" composition such as poloxamers and aceylated monoglycerides are not needed to prepare the sponge according to the preceding method.

DETAILED DESCRIPTION OF THE INVENTION

Figure 1A:
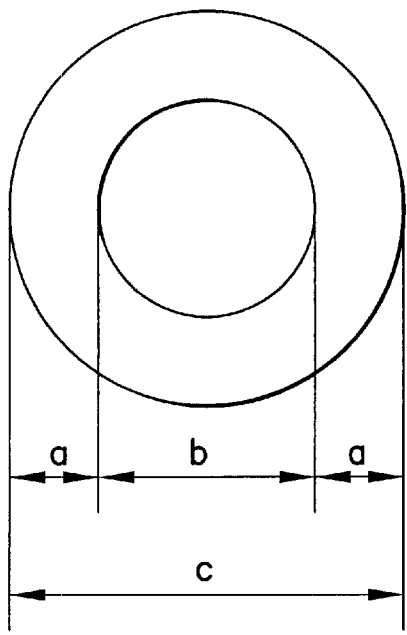
FIG. 1A is a plan view of a sponge according to the present invention having an outer diameter "c", an inner diameter "b" and sidewalls "a".

The present invention relates to bio-erodible microbicidal devices for prevention of STDs based on an acidic polymer which retains antiviral activity at neutral pH and thus does not lose activity in the presence of seminal fluid. Based on applicants, earlier studies, CAP and HPMCP meet these criteria (Neurath, A. R., Strick, N., Li, Y. -Y., Jiang, S., "Design of a 'Microbicide' for Prevention of Sexually Transmitted Diseases Using 'Inactive' Pharmaceutical Excipients", *Biologicals,* 27, 11–21, (1999); U.S. Pat. No. 5,985,313).

The present invention involves the use of a micronized compound, such as cellulose acetate phthalate (CAP) and/or hydroxypropylmethylcellulose phthalate (HPMCP).

Some of the properties of CAP as described in the *Handbook of Pharmaceutical Excipients* are summarized as follows:

Non proprietary Names:
BP: Cellacephate
PhEur: Cellulosi acetas phthalas
USPNF: Cellulose acetate phthalate Synonyms:

Acetyl phthalyl cellulose; CAP; cellacefate; cellulose acetate hydrogen 1,2-benzenedicarboxylate; cellulose acetate hydrogen phthalate; cellulose acetate monophthalate; cellulose acetophthalate; cellulose acetylphthalate.

Chemical Name and CAS Registry Number:

Cellulose, acetate, 1,2-benzenedicarboxylate [9004-38-0]

Cellulose acetate phthalate is a cellulose in which about half the hydroxyl groups are acetylated and about a quarter are esterified, with one of the two acid groups being phthalic acid. The other acid group is free. See the structural formula below.

Structural Formula:

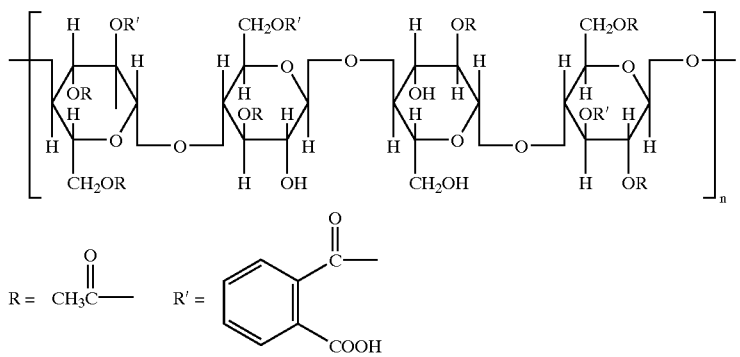

Functional Category: Coating Agent

Applications in Pharmaceutical Formulation or Technology:

Cellulose acetate phthalate has heretofore been used as an enteric film coating material, or as a matrix binder, for tablets and capsules (Spitael, J., Kinget, R., Naessens, K., "Dissolution Rate of Cellulose Acetate Phthalate and Brönsted catalysis Law", Pharm. Ind., (1980), 42:846–849; Takenaka, H., Kawashima, Y., Lin, S-Y., "Preparation of Enteric-Coated Microcapsules for Tableting by Spray-Drying Technique and in vitro Simulation of Drug Release from the Tablet in GI Tract", J. Pharm. Sci., (1980), 69:1388–1392; Stricker, I., Kulke, H., "Rate of Disintegration and Passage of Enteric-Coated Tablets in Gastrointestinal Tract", Pharm. Ind., (1981), 43:1018–1021; Takenaka, H., Kawashimna, Y., Lin, S-Y, "Polymorphism of Spray-Dried Microencapsulated Sulfamethoxazole with Cellulose Acetate Phthalate and Colloidal Silica Montmorillonite, or Talc", J. Pharm. Sci., (1981), 70:1256–1260; Maharaj, I., Nairn, J. G., Campbell J. B., "Simple Rapid method for the Preparation of Enteric-Coated Microspheres", J. Pharm. Sci., (1984), 73:39–42; Beyger, J. W., Nairn, J. G., "Some Factors Affecting the Microencapsulation of Pharmaceuticals with Cellulose Acetate Phthalate", J. Pharm. Sci., (1988), 75-573–578; Lin, S-Y, Kawashima, Y., "Drug Release from Tablets Containing Cellulose Acetate Phthalate as an Additive or Enteric-Coating Material", Pharm. Res., (1987), 4:70–74; Thoma, K. Hekenmüller, H., "Effect of Film Formers and Plasticizers on Stability of Resistance and Disintegration Behaviour, Part 4: Pharmaceutical-Technological and Analytical Studies of Gastric Juice Resistant Commercial Preparations", Pharmazie, (1987), 42:837–841).

Such coatings resist prolonged contact with the strongly acidic gastric fluid, but soften and swell in the mildly acidic or neutral intestinal environment.

Cellulose acetate phthalate, heretofore used as a pharmaceutical excipient, was commonly applied to solid dosage forms either by coating from organic or aqueous solvent systems, or by direct compression. Concentrations used were 0.5 to 9.0% of the core weight. The addition of plasticizers improves the water resistance of this coating material, and such plasticized films are more effective than when cellulose acetate phthalate is used alone as an adjuvant. Cellulose acetate phthalate is compatible with the following plasticizers: acetylated monoglyceride; butyl phthalylbutyl glycolate; dibutyl tartrate; diethyl phthalate; dimethyl phthalate; ethyl phthalyethyl glycolate; glycerin; propylene glycol; triacetin; triacetin citrate and tripropionin. Cellulose acetate phthalate has also been used heretofore in combination with other coating agents to control drug release, e.g., ethylcellulose.

Description:

Cellulose acetate phthalate is a hygroscopic, white, free-flowing powder or colorless flakes. It is tasteless and odorless, or may have a slight odor of acetic acid.

Pharmacopeial Specifications:

| Test | PhEur 1984 | USPNF XVII (Suppl 2) |
|---|---|---|
| Identification | + | + |
| Appearance of solution | + | − |
| Appearance of a film | + | − |
| Solubility of a film | + | − |
| Viscosity at 25° C. | − | 45–90 cP. |
| Water | ≦5.0% | ≦5.0% |
| Residue on ignition | − | ≦0.1% |
| Sulfated ash | ≦0.1% | − |
| Free acid | ≦3.0% | ≦6.0% |
| Heavy metals | ≦10 ppm | − |
| Phthalyl content | 30.0–40.0% | 30.0–36.0% |
| Acetyl content | 17.0–26.0% | 21.5–26.0% |

Typical Properties:

Hygroscopicity: cellulose acetate phthalate is hygroscopic and precautions are necessary to avoid excessive absorption of moisture (Callahan, J. C., Cleary, G. W., Elefant, M., Kaplan, G., Kensler, T., Nash, R. A., "Equilibrium Moisture Content of Pharmaceutical Excipients", Drug Dev. Ind. Pharm., (1982), 8:355–369).

Melting point: 192° C. Glass transition temperature is 160–170° C. (Sakellariou, P., Rowe, R. C., White, E. F. T., "The Thermomechanical Properties and Glass Transition Temperatures of Some Cellulose Derivatives used in Film Coating", Int. J. Pharmaceutics, (1985), 27:267–277).

Solubility: practically insoluble in alcohols, chlorinated hydrocarbons, hydrocarbons, and water; soluble in cyclic ethers, esters, ether alcohols, ketones and certain solvent mixtures. Also soluble in certain buffered aqueous solutions at greater than pH 6. The following list shows some of the solvents and solvent mixtures in which cellulose acetate phthalate has a solubility of 1 in 10 parts or more.

Acetone
Acetone: Ethanol (1:1)
Acetone: Methanol (1:1/1:3)
Acetone: Methylene chloride (1:1/1:3)
Acetone: Water (97:3)
Benzene: Methanol (1:1)
Diacetone alcohol Dioxane
Ethoxyethyl acetate
Ethyl acetate: Ethanol (1:1)
Ethyl acetate: Propan-2-ol (1:1/1:3)
Ethylene glycol monoacetate
Ethyl lactate
Methoxyethyl acetate
β-Methoxyethylene alcohol
Methyl acetate
Methylene chloride: Ethanol (3:1)
Methyl ethyl ketone Viscosity (dynamic): 50–90 mPas (50–90 cP) for a 15% w/w solution in acetone with a moisture content of 0.4%. This is a good coating solution with a honey-like consistency, but the viscosity is influenced by the purity of the solvent.

Stability and Storage Conditions:

Cellulose acetate phthalate hydrolyzes slowly under prolonged adverse conditions, such as high temperature and humidity, with a resultant increase in free acid content, viscosity and odor of acetic acid. If its moisture content is above about 6% w/w, fairly rapid hydrolysis occurs. However, cellulose acetate phthalate is stable if stored in a well-closed container in a cool, dry place.

Incompatibilities:

Cellulose acetate phthalate is incompatible with ferrous sulfate, ferric chloride, silver nitrate, sodium citrate, aluminum sulfate calcium chloride, mercuric chloride, barium nitrate, basic lead acetate, and strong oxidizing agents such as strong alkalis and acids. It should be noted that one carboxylic acid group of the phthalic acid moiety remains unesterified and free for interactions. Accordingly, incompatibility with acid sensitive drugs may occur (Rawlins E. A., editor, "Bentley's Textbook of Pharmaceutics", London: Baillière, Tindall and Cox, (1977), 291).

Method of Manufacture:

Cellulose acetate phthalate is produced by reacting the partial acetate ester of cellulose with phthalic anhydride in the presence of a tertiary organic base, such as pyridine.

Safety:

Cellulose acetate phthalate is widely used in oral pharmaceutical products and is generally regarded as a nontoxic material, free of adverse effects.

Results of long-term feeding studies with cellulose acetate phthalate, in rats and dogs, have indicated a low oral toxicity. Rats survived daily feedings of up to 30 in the diet for up to one year without showing a depression in growth. Dogs fed 16 g daily in the diet for one year also remained normal (Hodge, H. C., "The Chronic Toxicity of Cellulose Acetate Phthalate in Rats and Dogs", *J. Pharmacol.*, 80, 250–255, (1944)).

Regulatory Status:

Included in the FDA Inactive Ingredients Guide (oral capsules and tablets). Included in nonparenteral medicines licensed in the United Kingdom.

Pharmacopeias: Aust, Br, Braz, Cz, Eur, Fr, Ger, Gr, Hung, Ind, It, Jon, Mex, Neth, Nord, Port, Swiss and USPNF.

Some of the properties of HPMCP, described in the *Handbook of Pharmaceutical Excipients* are summarized as follows:

Non proprietary Names: BP: Hypromellose phthalate; PhEur: Methylhydroxypropylcellulosi phthalas and USPNF: Hydroxypropyl-methylcellulose phthalate.

Synonyms: Cellulose phthalate hydroxypropyl methyl ether; HPMCP; 2-hydroxypropylmethylcellulose phthalate; methylhydroxypropylcellulose phthalate.

Chemical Name and CAS Registry Number: Cellulose, hydrogen 1,2-benzenedicarboxylate, 2-hydroxypropyl methyl ether [9050-31-1]

Structural Formula:

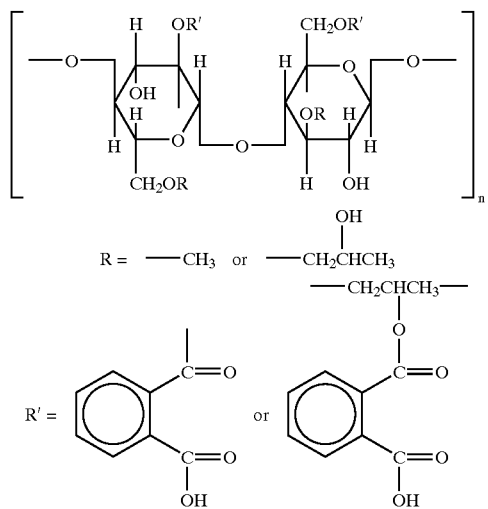

Functional Category: Coating Agent.

Applications in Pharmaceutical Formulations or Technology

Hydroxypropylmethylcellulose phthalate has heretofore been widely used in oral pharmaceutical formulations as an enteric coating material for tablets or granules (Ehrhardt, L., Patt, L., Schindler, E., "Optimization of Film Coating Systems", *Pharm. Ind.*, (1973), 35:719–722; Delporte, J. P., Jaminet, F., "Influence of Formulation of Enteric-Coated Tablets on the Bioavailability of the Drug", *J. Pharm. Belg.*, (1976), 31-263–276; Patt, L., Hartmann V., "Solvent Residues Film Forming Agents", *Pharm. Ind.*, (1976), 38:902–906; Stafford, J. W., "Enteric Film Coating Using Completely Aqueous Dissolved Hydroxypropyl Methylcellulose Phthalate Spray Solutions", *Drug. Dev Ind. Pharm.*, (1982), 8:513–530; Thoma, K., Heckenmüller, H., Oschmann, R., "Resistance and Disintegration Behaviour of Gastric Juice Resistant Drugs", *Pharmazie*, (1987), 42:832–836; Thoma, K., Heckenmüller, H., Oschmann, R., "Impact of Film Formers and Plasticizers on Stability of Resistance and Disintegration Behaviour", *Pharmazie*, (1987), 42:837–841).

Hydroxypropylmethylcellulose phthalate is insoluble in gastric fluid, but will swell and dissolve rapidly in the upper intestine. Generally, concentrations of 5–10% of hydroxypropylmethylcellulose phthalate were employed with the material being dissolved in either a dichloromethane: ethanol (50:50) or an ethanol: water (80:20) solvent mixture. Hydroxpropylmethylcellulose phthalate can normally be applied to tablets and granules without the addition of a plasticizer or other film formers, using established coating techniques (Rowe, R. C., "Molecular Weight Studies on the Hydroxypropyl Methylcellulose Phthalate (HP55)", *Acta. Pharm. Technol.*, (1982), 28(2):127–130. However, the addition of a small amount of plasticizer or water can avoid film cracking problems; many commonly used plasticizers such as diacetin, triacetin, diethyl and dibutyl phthalate, castor oil, acetyl monoglyceride and polyethylene glycols are compatible with hydroxypropylmethylcellulose phthalate. Tablets coated with hydroxypropylmethylcellulose phthalate disintegrate more rapidly than tablets coated with cellulose acetate phthalate.

Hydroxypropylmethylcellulose phthalate can be applied to tablet surfaces using a dispersion of the micronized hydroxypropylmethylcellulose phthalate powder in an aqueous dispersion of a suitable plasticizer such as triacetin, triethyl citrate or diethyl tartrate along with a wetting agent (Muhammad, N. A., Boisvert, W., Harris, M. R., Weiss, J., "Evaluation of Hydroxypropyl Methylcellulose Phthalate 50 as Film Forming Polymer from Aqueous Dispersion Systems", *Drug Dev. Ind. Pharm., (1992)*, 18:1787–1797).

Hydroxypropylmeclylcellulose phthalate may be used alone or in combination with other soluble or insoluble binders in the preparation of granules with sustained drug release properties; the release rate is pH dependent. Since hydroxypropyl-methylcellulose phthalate is tasteless and insoluble in saliva, it can be used as a coating to mask the unpleasant taste of some tablet formulations.

Description:

Hydroxypropylmethylcellulose phthalate occurs as white to slightly off-white colored free-flowing flakes or as a granular powder. It is odorless or with a slightly acidic odor, and a barely detectable taste.

Typical Properties:

Melting point: 150° C.

Solubility: practically insoluble in ethanol and water; very slightly soluble in acetone, and toluene; soluble in aqueous alkalis, a mixture of equal volumes of acetone and methanol, and in a mixture of equal volumes of dichloromethane and methanol.

Stability and Storage Conditions:

Hydroxypropylmethylcellulose phthalate is chemically and physically stable at ambient temperature and humidity for 3–4 years, and for 2 to 3 months at 40° C. and 75% relative humidity (Shin-Etsu Chemical Co., Ltd., Technical Literature: Hydroxypropyl Methylcelluose Phthalate, (1993). Hydroxypropylmethylcellulose phthalate is stable on exposure to UV light for up to 3 months at 25° C. and 70% relative humidity (Shin-Etsu Chemical Co., Ltd., Technical Literature: Hydroxypropyl-Methylcelluose Phthalate, (1993). In general, hydroxypropylmethylcellulose phthalate is more stable than cellulose acetate phthalate. At ambient storage conditions, hydroxypropylmethylcellulose phthalate is not susceptible to microbial attack.

Incompatibilities:

Incompatible with strong oxidizing agents. Splitting of film coatings has been reported rarely, most notably with coated tablets which contain microcrystalline cellulose and calcium carboxymethylcellulose. Film splitting has also occurred when a mixture of acetone: propan-2-ol or dichloromethane: propan-2-ol has been used as a coating solvent, or when coatings have been applied in conditions of low temperature and humidity. However, film splitting may be avoided by careful selection of the coating solvent used, by using a higher molecular weight grade of polymer (Rowe, R. C., "Molecular Weight Studies on the Hydroxypropyl Methylcellulose Phthalate (HP55), *Acta. Pharm. Technol., (1982)*, 28(2):127–130), or by the addition of a plasticizer, such as acetyl monoglyceride or triacetin. The addition of more than about 10% titanium dioxide to a coating solution of hydroxypropylmethylcellulose phthalate, that is used to produce a colored film coating, may result in coatings with decreased elasticity and gastric fluid resistance (Shin-Etsu Chemical Co., Ltd., Technical Literature: Hydroxypropyl Methylcellulose Phthalate, (1993)).

Method of Manufacture:

Hydroxypropylmethylcellulose acetate phthalate is prepared by the esterification of hydroxypropylmethylcellulose with phthalic anhydride. The degree of methoxy and phthalyl substitution determines the properties of the polymer and in particular the pH at which it dissolves in aqueous media.

Safety:

Hydroxypropylmethylcellulose phthalate has been heretofore widely used, primarily as an enteric coating agent, in oral pharmaceutical formulations. Chronic and acute animal feeding studies on several different species have shown no evidence or teratogenicity or toxicity associated with hydroxypropylmethylcellulose phthalate (Kitagawa, H., Kawana, H., Satoh, T., Fukuda, Y., "Acute and Subacute Toxicities of Hydroxypropyl Methylcellulose Phthalate", *Pharmacometrics, (1970)*, 4(6):1017–1025; Kitagawa, H., Satoh, T., Yokoshima, T., Nanbo, T., "Absorption, Distribution and Excretion of Hydroxypropyl Methylcellulose Phthalate in the Rat", *Pharmacometrics, (1971)*, 5(1):1–4; Ito, R., Toida, S., "Studies on the Teratogenicity of a New Enteric Coating Material, Hydroxypropyl Methylcellulose Phthalate (HPMCP) in Rats and Mice", *J. Med. Soc. Toho-Univ., (1972)*, 19(5):453–461; Kitagawa, H., Yano, H., Fukuda, Y., "Chronic Toxicity of Hydroxypropylmethylcellulose Phthalate in Rats", *Pharmacometrics, (1973)*, 7(5);689–701; Kitagawa, H., Yokoshima, T., Nanbo, T., Hasegawa, M., "Absorption, Distribution, Excretion and Metabolism of $^{14}$C-hydroxypropyl Methylcellulose Phthalate", *Pharmacometrics, (1974)*, 8(8):1123–1132. Hydroxypropylmethylcellulose phthalate is generally regarded as a nonirritant and nontoxic material.

$LD_{50}$ (rat, oral): >15 g/kg (Kitagawa et al., *Pharmacometrics, (1970)*, 4(6):1017–1025).

Regulatory Status: included in the FDA Inactive Ingredients Guide (oral capsules and tablets) and included in nonparenteral medicines licensed in the United Kingdom.

Pharmacopeias: Br, Eur, Fr, Gr, It, Jpn, Neth, Port, Swiss and USPNF.

Related Substances: cellulose acetate phthalate; Hydroxypropyl-Methylcellulose.

Hydroxypropylmethylcellulose phthalate can be dissolved in the following solvents:

Acetone: ethanol
Acetone: methanol
Acetone: water (95:5)
Benzene: methanol
Dichloromethane: ethanol
Dichloromethane: methanol
Dioxane
Ethyl acetate: methanol A particularly preferred micronized preparation for use in the present invention contains micronized CAP and/or micronized HPMCP, or micronized CAP containing other ingredients (a mixture of CAP, a poloxamer and acetylated monoglycerides such as sold by the FMC Corporation under the trade name "AQUATERIC"). A poloxamer is a nonionic polyoxyethylene-polyoxypropylene copolymer.

The chemical name for a poloxamer is α-hydro-ω-hydroxypoly-(oxyethylene) poly(oxypropylene) poly (oxyethylene) block copolymer. The poloxamer polyols are a series of closely related block copolymers of ethylene oxide and propylene oxide conforming to the following formula:

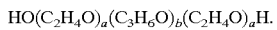

The term "micronized" used herein refers to particles having a particle size of less than 35 microns, preferably less than 15 microns, more preferably less than 10 microns and most preferably less than 5 microns.

CAP is commonly used as an enteric film coating material or as a matrix binder for tablets and capsules. Its safety has been extensively studied and it has been shown to be free of adverse effects. Vaginal irritation tests in the rabbit model further confirmed its safety.

The present invention is particularly directed to a soft solid insertable device based on CAP and/or HPHCP. This proved to be difficult to accomplish since CAP is insoluble at low pH, including normal vaginal pH in humans, and solid materials made of CAP are hard, brittle and thus unsuitable for the desired purpose. Furthermore a device generated from CAP would have only a limited surface area available for antiviral/antimicrobial action and would not be likely to be sufficiently effective as a microbicidal device.

To overcome the aforesaid difficulty, applicants employed micronized CAP and/or HPHCP, including a micronized composition, "AQUATERIC", containing 66 to 73 weight a CAP, a polyoxyethylene-polyoxypropylene block copolymer and distilled acetylated monoglycerides (FMC, Philadelphia, Pa.); (Neurath, A. R., Strick, N., Li, Y. -Y., Jiang, S., "Design of a 'Microbicide' for Prevention of Sexually Transmitted Diseases Using 'Inactive' Pharmaceutical Excipients", *Biologicals*, 27, 11–21, (1999); U.S. Pat. No. 5,985,313; Gyotoku, T., Aurelian, L., Neurath, A. R., "Cellulose Acetate Phthalate (CAP): An 'Inactive' Pharmaceutical Excipient With Antiviral Activity in the Mouse Model of Genital Herpesvirus Infection", *Antiviral Chemistry & Chemotherapy*, 10, 327–332). This micronized form of CAP was incorporated into sponge-like materials made from other cellulose derivatives, hydroxypropylmethylcellulose ("HPMC") and/or methylcellulose ("MC") by foam generating and freeze-drying processes.

Surprisingly, it was found not only that micronized CAP/ "AQUATERIC" can be incorporated into solid foams/ sponges generated from HPMC and/or MC, but that such sponges were soft, mechanically resilient and thus ideally suitable as bio-erodible microbicidal vaginal devices. Even more surprisingly, the CAP/"AQUATERIC" not only endows the dried sponges with mechanical resilience, but upon bioerosion initiated by exposure to water, micronized CAP/"AQUATERIC", in its original micronized form, is released from the sponges and thus fully exerts its antiviral/ antimicrobial activities. Thus, incorporation of micronized CAP/"AQUATERIC" into the sponges provides not only virucidal and microbicidal properties to the sponges (as described for micronized CAP hereinbefore), but most unexpectedly also provided the sponges with highly desirable mechanical properties, without the need for any ingredients other than the aforementioned cellulose derivatives.

The composition of the foams can be altered by varying the concentrations of CAP and of HPMC and MC and their respective viscosities in such a way that the final properties of the sponges are most desirable. This also depends on the foaming equipment as well as freeze-drying. The optimal conditions can be easily determined by those of ordinary skill in the art. To further scale-up the production of the sponges, equipment for foaming and freeze-drying described in U.S. Pat. No. 5,863,553 (the entire contents of which are hereby incorporated by reference herein) or any alternative equipment available from several different companies internationally can be used.

The "AQUATERIC" composition that is used in the preparation of the CAP-based sponges described hereinabove is a micronized powder, which contains, in addition to CAP (such as approximately 67–70 wt. % CAP), poloxamers and distilled acetylated monoglycerides. The latter two compounds do not contribute to antiviral/virucidal activity. Therefore it is preferable to develop sponges, which contain only a micronized form of CAP, without such other ingredients. Micronization of commercially available CAP granules is not easily feasible in large scale. Similarly, other micronization processes, e.g., an emulsion diffusion process (Quintanar-Guerrero, D., Allémann, E., Fessi, H., and Doelker, E., "Pseudolatex Preparation Using a Novel Emulsion-Diffusion Process Involving Direct Displacement of Partially Water-Miscible Solvents by Distillation", *Intl. J. Pharmaceutics*, (1999), 188, 155–164) are expensive and cumbersome. The emulsion diffusion process utilizes emulsions generated by a combination of organic solvents (in which CAP has been dissolved) with water; the organic solvent is then removed by evaporation, resulting in a water suspension of micronized CAP. Surprisingly, applicants discovered that this emulsion diffusion process can be combined with foam formation, freezing and freeze-drying, resulting, if an appropriate mold (see FIGS. 1A to 1C) is used for freezing and freeze-drying, in virucidal/ microbicidal sponges similar to those described above and prepared from the "AQUATERIC" composition. Surprisingly, the organic solvent does not interfere with the freezing and freeze-drying processes, nor does it adversely affect equipment used in the freeze-drying process.

Figure 1B:
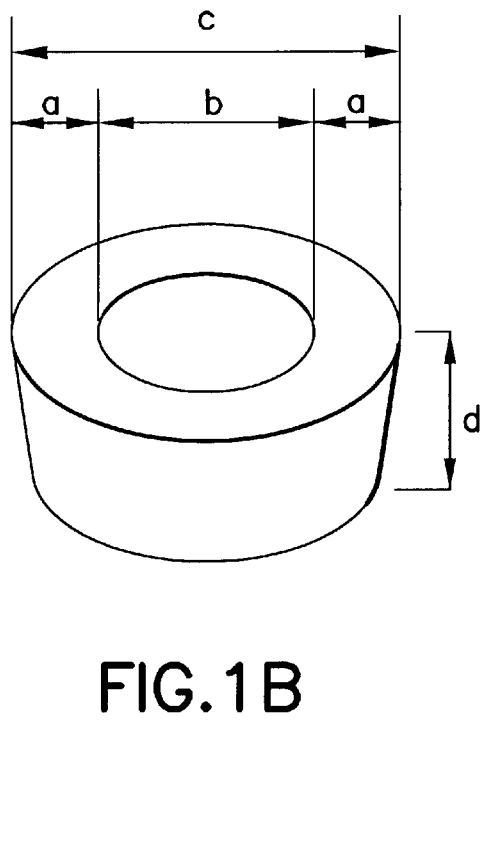
FIG. 1B is a perspective side view of the sponge depicted in FIG. 1A, wherein "d" is the height of the sponge.
Figure 1C:
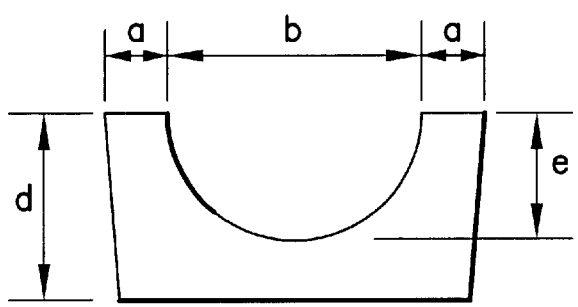
FIG. 1C is a sectional elevational view of the sponge depicted in FIGS. 1A and 1B, wherein "e" is the depth of the sponge.

In the sponges depicted in FIGS. 1A to 1C, the outer diameter "c" can be approximately 4.6 cm, the inner diameter "b" can be approximately 2.4 cm, and the sidewalls "a" can each be approximately 1.1 cm. The height "d" of the sponge shown in FIGS. 1B and 1C can be approximately 2.25 cm. The depth "e" of the sponge shown in FIG. 1C can be approximately 1.25 cm. FIG. 1C shows the taper of the sidewalls wherein there is a slight slope inward from bottom to top at an angle which can be approximately 10°.

For protection against environmental deterioration (humidity, etc.), the sponges can be stored in round plastic containers of suitable dimension or can be packaged in blister pouches, or aluminum foil.

EXAMPLES

Example 1

A solution of HPMC (100 cps; Spectrum, New Brunswick, N.J.: 1 weight %) in distilled water was prepared. Subsequently MC (Spectrum; 4,000 cps) was added to a final concentration of 1 weight % and "AQUATERIC" was added to a final concentration of 3 weight %. The suspension was foamed using either a Caffe Froth foamer (Bonjour Pacheco, Calif.) or an ESGE (Switzerland) homogenizer M133/1281-0. The generated foam was distributed into molds (e.g., molds for baking muffins with a "TEFLON" lining to facilitate the ease of removal of the final sponges) and rapidly frozen. Subsequently the frozen foams in the molds were freeze-dried to remove all water. The end-product was a soft sponge suitable for vaginal insertion.

The composition of the foams can be altered by, for example, using 2 weight % HPMC (4,000 cps) or 1 weight % HPMC (4,000 cps) combined with 1 weight % MC (400 cps). Other combinations of HPMC and MC of different viscosities can be used as long as the sponge remains soft and has not become brittle. The concentration of "AQUATERIC" was maintained at 1 to 5 weight %, preferably at 3 weight %.

Example 2

Sponges are prepared from inexpensive and commercially available CAP (Eastman Chemical Company, Kingsport, Tenn.) by the following procedure: 8 volumes of 0.75% methylcellulose (viscosity=400 cps) and 0.75% methylcellulose (viscosity=4,000 cps) in water (first solution) are mixed with 2 parts of a 10 weight % solution of CAP in ethyl acetate containing 5 volume % ethanol (second solution). The resultant emulsion is foamed, frozen and further treated as described herein for sponges based on the "AQUA-TERIC" composition. The mechanical and other properties of the sponges (softness, etc.) can be controlled by varying the concentrations of the methylcelluloses and the CAP. The optimal range of concentrations for the methylcelluloses in the first solution being 0.4 to 1.5 weight % each, and for CAP 2 to 15 weight a in ethyl acetate containing 5 volume % ethanol (second solution).

Example 3

Figure 2:
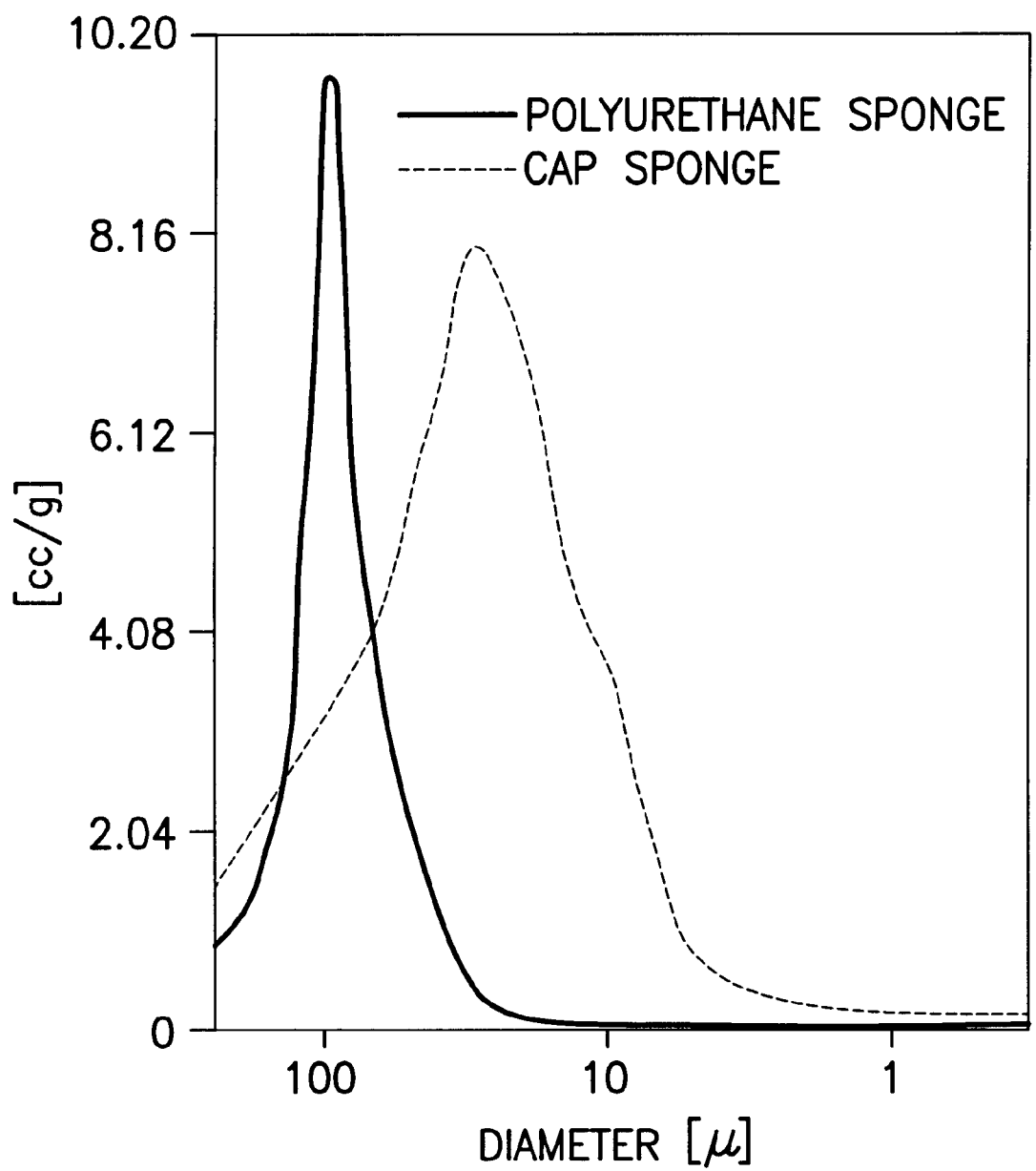
FIG. 2 is a graph showing mercury porosimetry of a polyurethane sponge and a CAP sponge according to the present invention.

To gain insight into the physical properties of the CAP sponges, as compared with currently available polyurethane sponges sold as contraceptive products over the counter ("OTC"), the pore size of CAP sponges was compared to that of the "TODAY" polyurethane sponge (Allendale Pharmaceuticals, Inc. Allendale, N.J.) using high pressure mercury porosimetry. The results shown in FIG. 2 indicated that the average pore size of the CAP sponges is substantially smaller than that of the polyurethane "TODAY" sponge, indicating that the CAP sponge is less likely to allow passage of virus infected cells. Furthermore, the CAP sponge by itself provides a low pH (acidic) environment without the need for any additional ingredient, to cause the lysis of infected cells followed by inactivation of the released virus particles. This cannot be accomplished using the polyurethane sponge, which by itself is inert, and requires the presence of a detergent to become virucidal and spermicidal. This expectation was borne out in experiments: MT2 cells ($2 \times 10^6$ cells in 0.3 ml were applied to a CAP sponge disc (300 mg), packed in a chromatographic column. The sponge disc was washed with 0.14 M NaCl containing 100 µg/ml of bovine serum albumin (BSA). Only 1.65% of cells originally placed on top of the sponges were recovered in the column effluent, indicating a 98.35% retention/inactivation of the added cells.

Example 4

Figure 3:
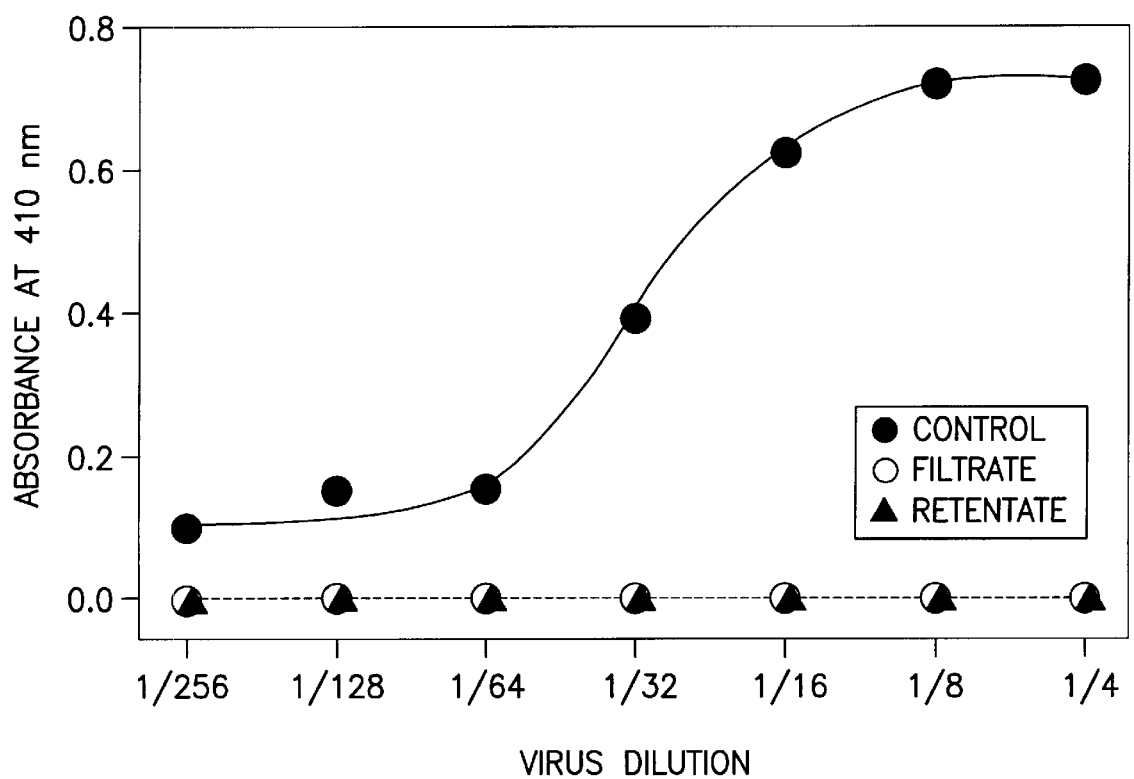
FIG. 3 is a graph showing that HIV-1 passing through CAP sponges according to the present invention becomes inactivated.

To determine whether cell-free human immunodeficiency virus type 1 (HIV-1) would become inactivated during passage through/contact with the sponges, the following experiment was carried out: 0.5 ml of tissue culture fluid containing infectious HIV-1 was mixed with an equal volume of 0.14 M NaCl containing 100 µg/ml BSA, and the mixture was applied to a sponge disc (167 mg) and the disc was subsequently washed with the same solution. Samples (ten) of 1 ml were collected and subsequently tested for HIV-1 infectivity. The residual sponge material within the chromatograhic column was resuspended in the same solution, centrifuged and the supernatant fluid was tested for HIV-1 infectivity. Tests for infectious HIV-1 were carried out, using HeLa-CD4-LTR/β-GAL cells plated in 96-well plates at $1 \times 10^4$ cells per well. Details of the test are as described in Neurath, A. R.; Jiang, S.; Strick, N.; Lin, K.; Li, Y. -Y.; and Debnath, A., "Bovine β-Lactoglobulin Modified by 3-Hydroxyphthalic Anhydride Blocks the CD4 Cell Receptor for HIV", *Nature Medicine,* (1996), 2 (2):230–234. Results shown in FIG. 3 indicate that the sponge inactivated HIV-1 infectivity.

Figure 4:
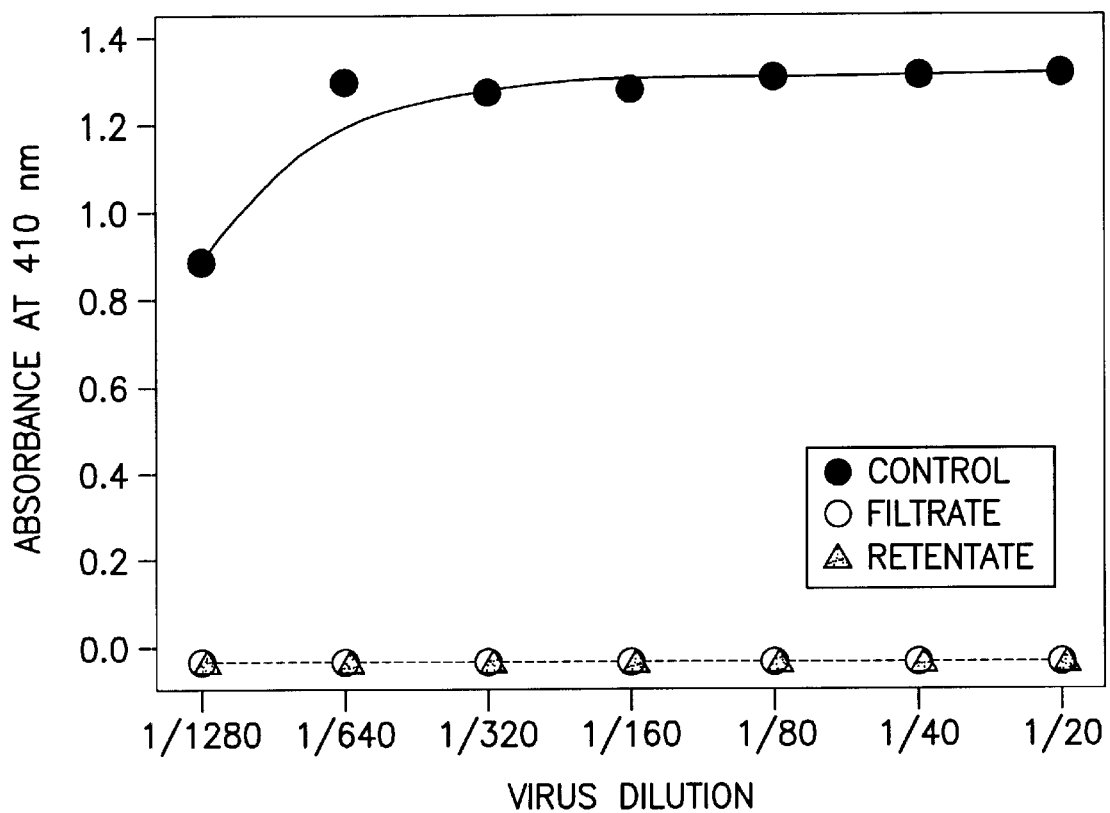
FIG. 4 is a graph showing that HSV-1 passing through CAP sponges according to the present invention become inactivated.

Similar experiments under the same conditions were carried out with a recombinant herpesvirus type 1 (HSV-1) vgCL5 expressing the gene for βGAL (Neurath, A. R.; Strick, N.; Li, Y. -Y.; Lin, K.; and Jiang, S., "Design of a 'Microbicide' for Prevention of Sexually Transmitted Diseases Using 'Inactive' Pharmaceutical Excipients", *Biologicals,* (1999), 27, 11–21). Passage through the column containing the CAP sponge resulted in complete inactivation of HSV-1 (FIG. 4).

Example 5

Figure 5:
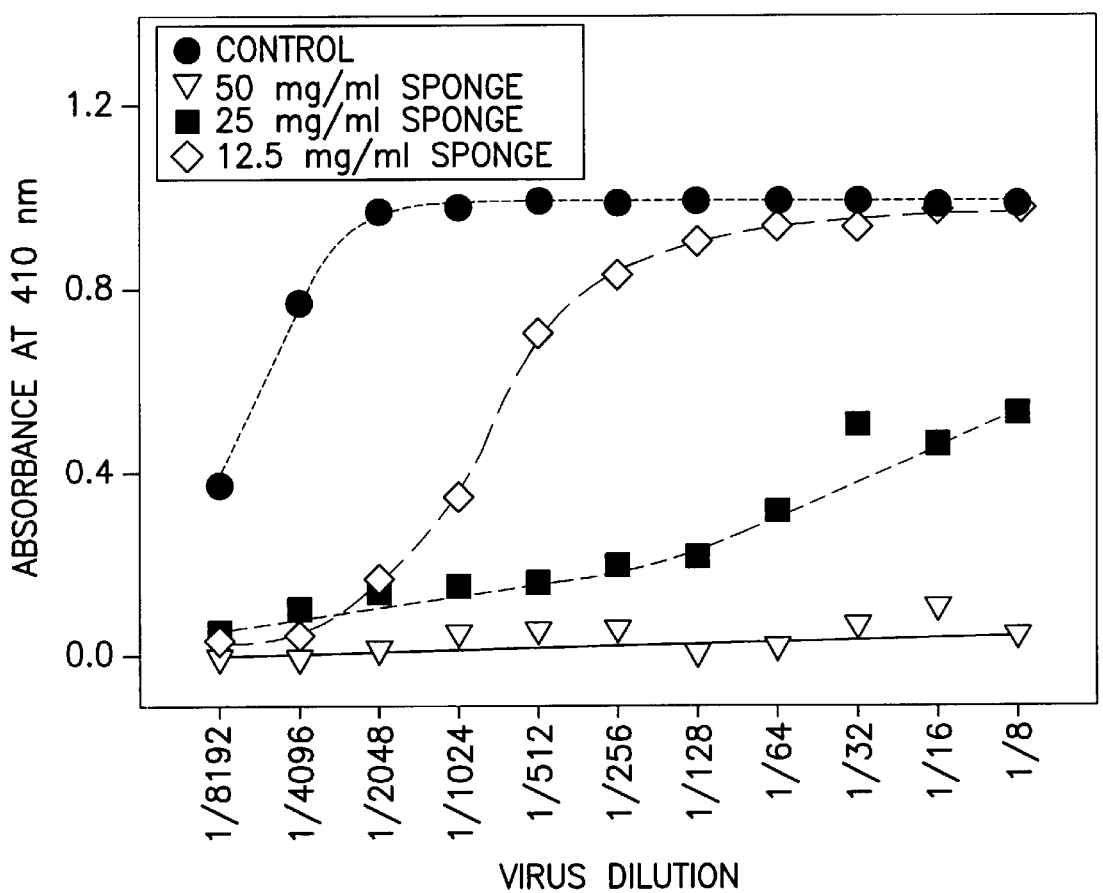
FIG. 5 is a graph showing inactivation of HSV-1 by CAP/"AQUATERIC" sponges according to the present invention.

To determine the relationship between the quantity of sponge material added to infectious tissue culture medium, graded quantities of the sponge were suspended in 0.5 ml of 0.14 M NaCl and mixed with an equal volume of tissue culture medium containing HSV-1 vgCL5 for 5 minutes at 37° C. After centrifugation, the supernatant fluid was tested for infectivity at serial twofold dilutions, similar dilutions being done with control virus not exposed to the sponge. The dilutions (100 µl) were added to an equal volume of Vero cells ($10^6$/ml) and incubated at 37° C. for 20 hours. The cells were lysed and β-Galactosidase determined spectrophotometrically as described in Neurath, A. R.; Strick, N.; Li, Y. -Y.; Lin, K.; and Jiang, S., "Design of a 'Microbicide' for Prevention of Sexually Transmitted Diseases Using: 'Inactive' Pharmaceutical Excipients", *Biologicals,* (1999), 27, 11–21. Results shown in FIG. 5 indicate complete inactivation of HSV-1 by the sponge at 50 mg/ml. Decreasing amounts of the added sponge material resulted in less effective virus inactivation.

Figure 6:
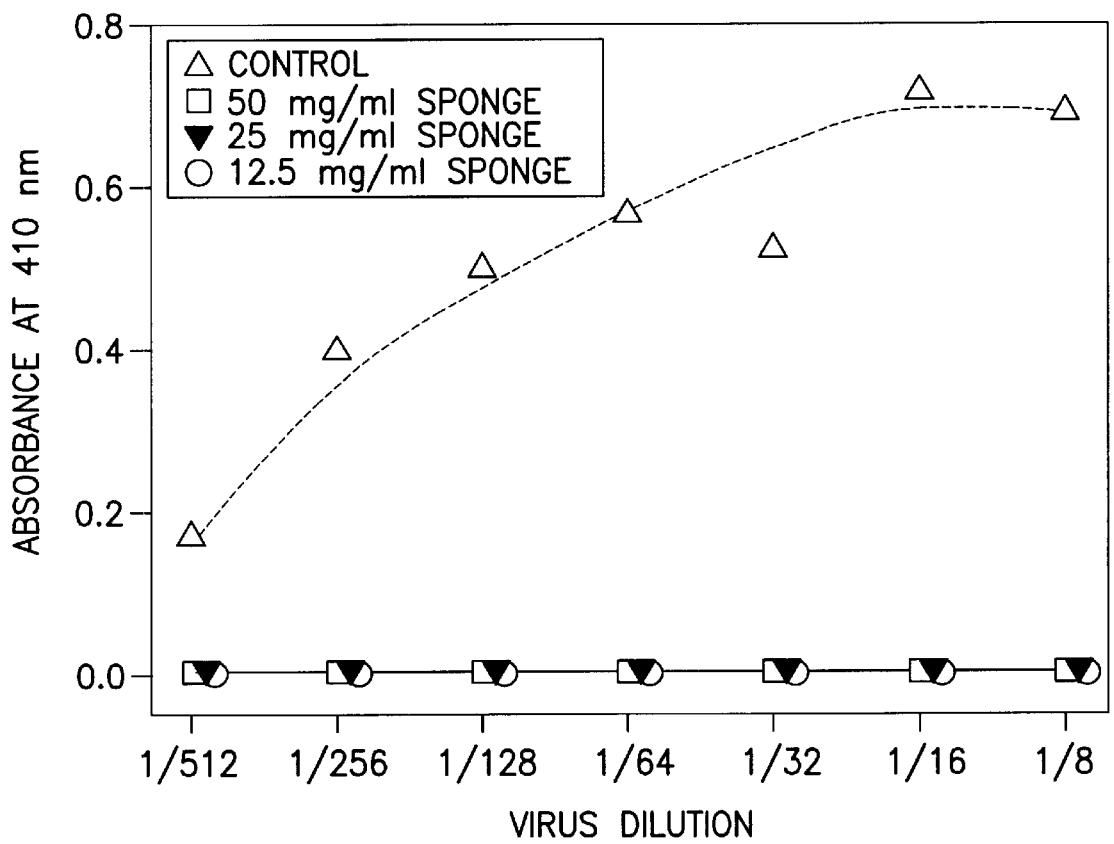
FIG. 6 is a graph showing inactivation of HSV-2 by CAP/"AQUATERIC" sponges according to the present invention.

Similar experiments under the same conditions were carried out with HSV-2, the type of herpesvirus most frequently transmitted sexually. In this case, the sponge-treated virus material and control virus were titered for infectivity using ELVIS cells, which express β-Galactosidase upon infection with HSV-2 (Neurath, A. R.; Strick, N.; Li, Y. -Y.; Lin, K.; and Jiang, S., "Design of a 'Microbicide' for Prevention of Sexually Transmitted Diseases Using: 'Inactive' Pharmaceutical Excipients, *Biologicals,* (1999), 27, 11–21). In this case, complete inactivation of HSV-2 infectivity was observed at all levels of sponge material added to virus suspensions (FIG. 6).

It will be appreciated that the instant specification is set forth by way of illustration and not limitation, and that various modifications and changes may be made without departing from the spirit and scope of the present invention.

What is claimed is:

1. An intravaginal bio-erodible microbicidal barrier device comprising
   (a) at least one micronized compound selected from the group consisting of cellulose acetate phthalate and hydroxypropylmethylcellulose phthalate, and
   (b) at least one water soluble or water dispersible cellulose compound selected from the group consisting of hydroxypropylmethylcellulose, methylcellulose, hydroxyethylcellulose, hydroxypropylcellulose, hydroxyethylmethylcellulose, hydroxyethylethylcellulose and hydroxypropylethylcellulose.

2. The device of claim 1, wherein the micronized compound comprises particles of a particle size of less than 35 microns.

3. The device of claim 1, wherein the micronized compound comprises particles of a particle size of less than 15 microns.

4. The device of claim 1, wherein the micronized compound comprises particles of a particle size of less than 10 microns.

5. The device of claim 1, wherein the micronized compound comprises particles of a particle size of less than 5 microns.

6. The device of claim 1, wherein the at least one micronized compound is cellulose acetate phthalate which is contained in a mixture which further comprises a polyoxyethylene-polyoxypropylene block copolymer and distilled acetylated monoglycerides.

7. The device of claim 1, wherein the at least one micronized compound consists essentially of cellulose acetate phthalate.

8. The device of claim 1, wherein the at least one micronized compound consists essentially of hydroxypropylmethylcellulose phthalate.

9. The device of claim 1, wherein the device is a vaginal sponge.

10. The device of claim 9, wherein the at least one water soluble or water dispersible cellulose compound consists essentially of both hydroxypropylmethylcellulose and methylcellulose.

11. The device of claim 9, wherein the at least one micronized compound consists essentially of cellulose acetate phthalate.

12. The device of claim 9, wherein the at least one micronized compound is cellulose acetate phthalate which is contained in a mixture which further comprises a polyoxyethylene-polyoxypropylene block copolymer and distilled acetylated monoglycerides.

13. The device of claim 9, wherein the at least one micronized compound consists essentially of hydroxypropylmethylcellulose phthalate.

14. A method of making an intravaginal bio-erodible microbicidal barrier device comprising:
(a) providing at least one micronized compound selected from the group consisting of cellulose acetate phthalate and hydroxypropylmethylcellulose phthalate; and
(b) adding to said at least one micronized compound, an aqueous solution of at least one water soluble or water dispersible cellulose compound selected from the group consisting of hydroxypropylmethylcellulose, methylcellulose, hydroxyethylcellulose, hydroxypropylcellulose, hydroxyethylmethylcellulose, hydroxyethylethylcellulose and hydroxypropylethylcellulose to form a suspension;
(c) foaming the suspension from step (b) to form a foam;
(d) disposing the foam from step (c) into a mold and freezing the foam to form a frozen foam; and
(e) freeze-drying the frozen foam from step (d) to remove water.

15. The method of claim 14, wherein the at least one micronized compound consists essentially of cellulose acetate phthalate and the at least one water soluble or water dispersible cellulose compound is selected from the group consisting of (a) hydroxypropylmethylcellulose, (b) methylcellulose and (c) both hydroxypropylmethylcellulose and methylcellulose.

16. The method of claim 15, wherein the mold has a shape for preparing a vaginal sponge.

17. The method of claim 14, wherein the at least one micronized compound consists essentially of hydroxypropylmethylcelluose phthalate and the at least one water soluble or water dispersible cellulose compound is selected from the group consisting of (a) hydroxypropylmethylcellulose, (b) methylcellulose and (c) both hydroxypropylmethylcellulose and methylcellulose.

18. The method of claim 17, wherein the mold has a shape for preparing a vaginal sponge.

19. A method of making an intravaginal bio-erodible microbicidal barrier device comprising:
(a) preparing a first solution and a second solution, the first solution comprising at least one water soluble or water dispersible cellulose compound selected from the group consisting of hydroxypropylmethylcellulose, methylcellulose, hydroxyethylcellulose, hydroxypropylcellulose, hydroxyethylmethylcellulose, hydroxyethylethylcellulose and hydroxypropylethylcellulose, suspended or dissolved in water; the second solution comprising at least one compound selected from the group consisting of cellulose acetate phthalate and hydroxypropylmethylcellulose phthalate, dissolved in at least one organic solvent;
(b) combining the first solution and the second solution to result in an emulsion in which the cellulose acetate phthalate or the hydroxypropylmethylcellulose phthalate is in a micronized form;
(c) foaming the suspension from step (b) to form a foam;
(d) disposing the foam from step (c) into a mold and freezing the foam to form a frozen foam; and
(e) freeze-drying the frozen foam from step (d) to remove water and to remove the organic solvent.

20. The method of claim 19, wherein the at least one compound selected from the group consisting of cellulose acetate phthalate and hydroxypropylmethylcellulose phthalate is cellulose acetate phthalate in a concentration of 2 to 15 weight W; and the organic solvent comprises ethyl acetate and ethanol.

* * * * *